United States Patent [19]

Buettner-Janz et al.

[11] Patent Number: 4,759,766
[45] Date of Patent: Jul. 26, 1988

[54] INTERVERTEBRAL DISC ENDOPROSTHESIS

[75] Inventors: Karin Buettner-Janz; Bernd Derr, both of Berlin; Klaus-Peter Erkel, Dresden; Hans-Joachim Helisch; Kurt Schellnack, both of Berlin; Roland Schumann, Dresden, all of German Democratic Rep.

[73] Assignee: Humboldt-Universitaet zu Berlin, Berlin, German Democratic Rep.

[21] Appl. No.: 96,314

[22] Filed: Sep. 9, 1987

Related U.S. Application Data

[63] Continuation of Ser. No. 767,552, Aug. 20, 1985, abandoned.

[30] Foreign Application Priority Data

Sep. 4, 1984 [DD] German Democratic Rep. ... 266959
Feb. 12, 1985 [DD] German Democratic Rep. ... 273192
Jul. 19, 1985 [DD] German Democratic Rep. ... 278792
Jul. 19, 1985 [DD] German Democratic Rep. ... 278793

[51] Int. Cl.$^4$ .............................................. A61F 2/44
[52] U.S. Cl. .................................... 623/17; 623/66
[58] Field of Search .................. 623/17, 11, 66, 16

[56] References Cited

U.S. PATENT DOCUMENTS 4,401,112 8/1983 Rezaian ........................... 623/17 X

FOREIGN PATENT DOCUMENTS 3023353 4/1981 Fed. Rep. of Germany ........ 623/17

Primary Examiner—Richard J. Apley
Assistant Examiner—Alan W. Cannon
Attorney, Agent, or Firm—Jordan and Hamburg

[57] ABSTRACT

An intervertebral disc endoprothesis comprises two symmetrical, concave end plates with an intermediate convex spacing piece. The end plates and the spacing piece have a plane guide rim. The end plates either have an edge shoulder or an annular groove for a toroid provided on the spacing piece. Alternatively, the intervertebral disc endoprothesis comprises two asymmetric end plates and a spacing piece, however, the two areas of movement are offset by 90° in relation to each other and are partial surfaces of a cylinder. In the third variation, the two symmetrical end plates are convex, the spacing piece is cylindrical as well as concave at the two ends and has a durable cover.

2 Claims, 6 Drawing Sheets

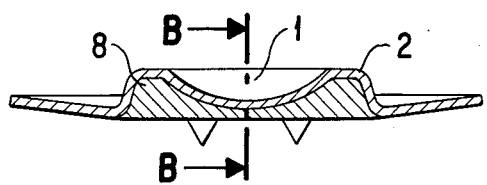
FIG. 6
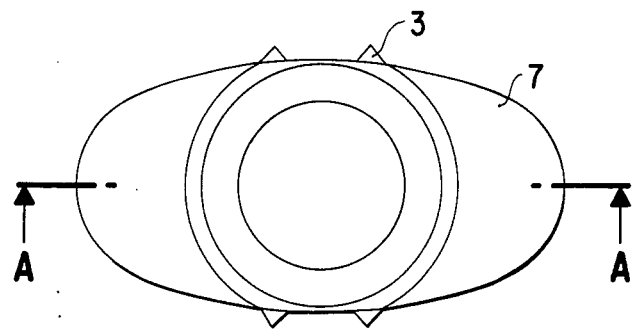
FIG. 5
FIG. 7
FIG. 9
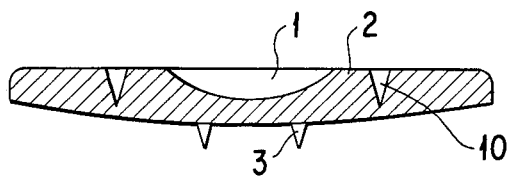
FIG. 8
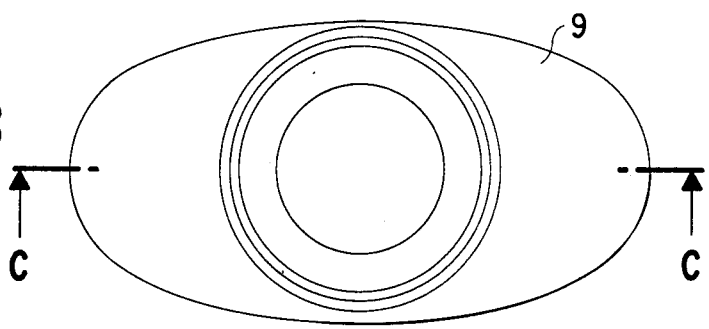

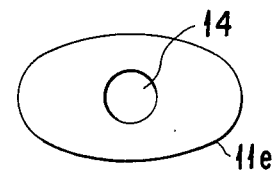
FIG. 13
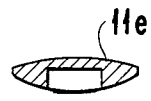
FIG. 15
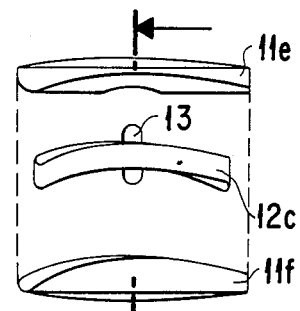
FIG. 12
FIG. 16
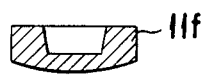
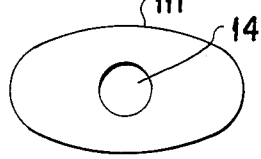
FIG. 14
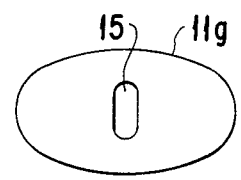
FIG. 18
FIG. 20
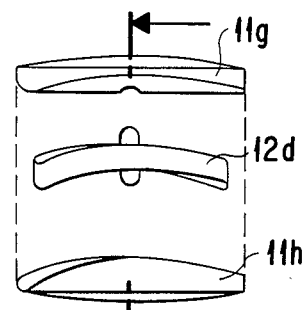
FIG. 17
FIG. 21
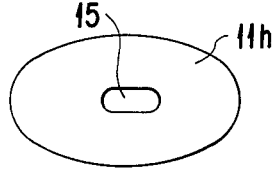
FIG. 19

INTERVERTEBRAL DISC ENDOPROSTHESIS

This application is a continuation of application Ser. No. 767,552, filed Aug. 20, 1985, now abandoned.

BACKGROUND OF THE INVENTION AND RELATED ART STATEMENT

The invention relates to an endoprothesis of the nucleus pulposus. The endoprothesis is inserted between the base plate and the cover plate of two adjacent vertebrae bodies (corpus vertebrae). The endoprothesis has multiple parts.

There are known a series of devices for replacing degenerated, damaged or destroyed intervertebral discs, or at least are intended for replaicng such discs. There are devices, as described in the U.S. Pat. No. 4,401,112, which insure only pressure absorbtion, without thereby restoring physiological mobility. It is known to replace a pathologically changed intervertebral disc, whereby the cavity resulting from the surgical removal of the nucleus pulposus is filled with silicone rubber which polymerizes out in situ. U.S. Pat. No. 4,349,921 describes a pin-shaped intervertebral disc prothesis. There are also known intervertebral disc prostheses of multiple parts made of metal. or combinations of metal and plastic material, or plastic material, each one consisting of an upper part and a lower part with a push-buttonlike, disc or spherical shaped intermediate piece (DE-PS No. 3,023,353; DE-OS No. 2,263,842; CH-PS No. 624,575; CH-PS No. 640,131). U.S. Pat. No. 4,309,777 and SU-PS No. 895,433 depict special constructions.

The known devices have the disadvantage of either not replacing the functions of a nucleus pulposus, or doing so only partially, or only insufficiently. Working cup-shaped support sockets into the spongiosa of the vertebrae bodies has the disadvantage of requiring to some extent protracted manipulations on the patient. Furthermore, it is not desirable that the outer layer of the vertebrae bodies, which is relatively hard in comparison to the spongiosa, is destroyed or perforated. Because of the great contact stresses, the irregular pressure distribution and/or the inflexibility of the materials, there is not only the danger of causing necrosis or bone resorptions, but the vertebrae bodies are also exposed to possible mechanical destruction. Further difficulties result from the surgical techniques which have to be used and from the fact that the safety requirements regarding positional changes are not met with the use of the intervertebral disc endoprothesis.

The object of the invention is to provide an endoprothesis of the nucleus pulposus providing utmost full value, which insures spacing maintenance or restoration and a physiological mobility in the affected section of the spinal column. Furthermore, it also has to be guaranteed operable over a long implant period at utmost safety in regard to positional changes.

The object of the invention is based on the technical problem of providing an endoprothesis of the nucleus pulposus which can be biochemically and biomechanically tolerated, which has stability of shape during pressure absorption, which can be implanted without sophisticated work on the adjacent vertebrae bodies, and which eliminates a mechanical destruction of the adjacent vertebrae bodies.

SUMMARY OF THE INVENTION

This technical problem is solved whereby the intervertebral disc endoprothesis consists of two end plates having an intermediate spacing piece. The interaction between the end plates and the spacing piece allows an approximately physiological extent of inclination of the vertebrae bodies. In a first embodiment of the invention, the spacing piece has a partially spherical surface and is of lenticular configuration, having a plane guide rim, and is provided on the outside with a toroid for preventing sliding off or slipping out of the end plates. The height of the spacing piece can vary according to the height of the space between the vertebrae.

The symmetrical end plates are concave at their center portions, they also have a plane guide rim integral with a shoulder provided with teeth. The size of the shoulder of the end plates is related to the sagittal curvature of the spinal column, so that the ventrodorsal difference of height of the space between the vertebrae can be taken into consideration. A ventral marking serves for simple orientation during the operation. The radius of curvature of the concave recess corresponds exactly to the radius of curvature of the spherical part of the spacing piece.

It is possible to provide the end plates at both lateral sides with laminar extensions, which are selected so that they occupy as large as possible an area of the base plate of the vertebra body or the top plate of the vertebra body. This results in a reduction of the compression stress per unit of area. This is especially advantageous for vertebrae bodies which can only be stressed at a reduced degree.

Additionally, or also separately, the contact surface of the end plates can be increased in that the cavity between the back side of the concave center portion and the offset guide rim is filled with a disc made of alloplastic material, which can also be bioactive. It is also conceivable to use bone cement. It is also possible to make the center portion of the end plates solid, i.e., without a cavity on the back side.

Finally, it is also possible to use solid material for the entire top plate. For that purpose, the concave center portion and an annular groove for receiving the toroid of a spacing piece are incorporated into a solid end plate, which makes contact with the base plate of the vertebra body or the cover plate of the vertebra body. The end plates and the spacing piece are made of materials approved for implant engineering; for instance, the end plates are made of noncorroding metal and the spacing piece is made of medical polyethylene or polyurethane of high compression and tension strengths. The reverse material combination is also possible. The use of other alloplastic materials, which can also be bioactive, is also possible. The contact areas of the end plates as well as the contact areas of the spacing piece are provided with high polish in order to minimize abrasion (low-friction principle).

For a safe implant anchoring the space between the vertebrae, teeth are provided on the edge and/or the surface of the bottom side of the end plates. It is possible to provide a bioactive coating for the teeth or the entire underside of the end plates. However, it is also possible to anchor the end plates with bone cement.

It is also possible to provide an intevertebral disc endoprothesis, wherein the upper and the bottom surfaces of the spacing piece, as well as the adjacent suraces of the end plates, correspond to surface segments of a cylinder with in each case equal radius of curvature of parts articulating with one another and with the plane of movement rotated by 90° from one articulation zone to another. The end plates are either round or somewhat oval, and the spacing piece is symmetrically smaller in relation thereof.

Depending on the location of the concave or convex curved surface of movement, the intervertebral disc endoprothesis functioning according to the "low-friction principle" can be manufactured in four different versions. The intervertebral disc endoprothesis can be executed varying in height according to the craniocaudal and ventrodorsal size of the intervertebral disc space. As an additional precaution against undesired positional changes of the center portion, it is possible to provide a cranially and caudially extending pin arranged at the middle of the center portion. This pin extends into recesses incorporated in the end plates. The recesses are advantageously either circular or slot-shaped. Conversely, pins of the end plate pointing towards the center of the segment, and bores in the center portion, or combined variations thereof, are also possible. In case of the latter variation, a rolling movement is carried out by one of the two movement zones, and a concurrent gliding movement by the other movement zone. During this movement process, the spacing piece changes its position and the end plates remain stably anchored to the vertebrae bodies, for instance, via teeth.

Finally, an intervertebral disc endoprothesis of which the two symmetrical end plates have convex center portions, and whereby the spacing piece is cylindrical and at both ends concave is also possible. The radii of curvature of the concave surfaces and of the convex surfaces are thereby equal. Additionally, the cylindrical spacing piece, which is made of polyethylene, is provided with a stable cover, so that the cold flow of the polyethylene, which can occur under the effect of a high pressure stress, can be prevented or limited. The cover is limited in its height so that is is smaller than the spacing piece, in order to avoid a direct contact with the end plates.

The convex center portion of the end plates can additionally be provided with pins which extend into the recesses of the spacing piece. The diameters of the recesses are designed so that they are larger than the diameters of the pins. Such a construction limits the maximum mobility of the intervertebral disc endoprothesis and represents an additional precaution against an unintentional positional change of the spacing piece.

For the purpose of radiological depiction, plastic parts which are not visible otherwise, can be appropriately marked.

The invention allows for the first time an approximately complete replacement of the nucleus pulposus and guarantees physiological mobility in the affected section of the spinal column.

BRIEF DESCRIPTION OF THE DRAWINGS

The invention will be more fully explained below with the help of examples, and the drawings pertaining thereto show the following:

FIG. 5 is a top plane view of an end plate with lateral extensions according to the invention;

FIG. 6 is a cross-section taken on section line A—A of FIG. 5;

FIG. 7 is a cross-section taken on section line B—B of FIG. 6;

FIG. 8 is a top plan view of a solid end plate according to the invention;

FIG. 9 is a cross-section taken on section line C—C of FIG. 8;

FIG. 12 is an exploded side elevation view of an intervertebral disc endoprothesis according to the invention, similar to those of FIGS. 10 and 11, however, provided with additional safety guard pins and circular openings;

FIGS. 13 and 14 are, respectively, top and bottom plan views of the endoprothesis of FIG. 11;

FIGS. 15 and 16 are cross-sections of the top and bottom end plates, respectively, taken on the section line shown in FIG. 12;

FIG. 17 is an exploded side elevation view of an intervertebral disc endoprothesis according to the invention, similar to those of FIGS. 10 and 11, however, provided with additional safety guard pins and slot-shaped openings;

FIG. 18 and 19 are, respectively, top and bottom plan views of the endoprothesis of FIG. 17;

FIGS. 20 and 21 are cross-sections of the top and bottom end plates, respectively, taken on the section line shown in FIG. 17;

DETAILED DESCRIPTION OF PREFERRED EMBODIMENTS

Example 1

Figure 1:
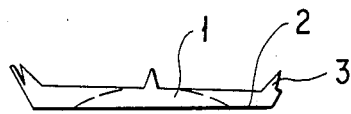
FIG. 1 is a side elevation of a top end plate according to the invention.
Figure 2:
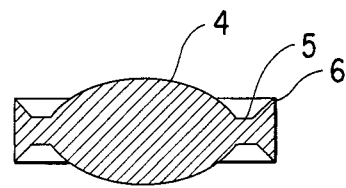
FIG. 2 is a radial cross-sectional view of a spacing piece according to the invention.
Figure 3:
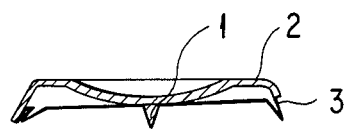
FIG. 3 is a radial cross-sectional view of a bottom end plate according to the invention, which is identical to the top end plate.
Figure 4:
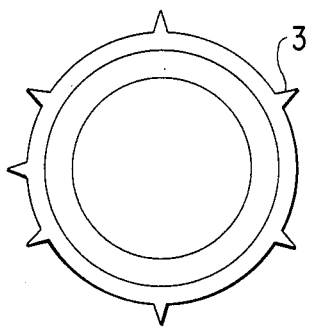
FIG. 4 is a top plan view of the end plate of FIG. 1.

The end plates shown in FIGS. 1, 3 and 4 are made of noncorroding metal and have a concave center portion 1 and an annular, plane guide rim 2. The offset edges of the end plates are provided with teeth 3, which guarantee a safe anchorage in the vertebrae bodies. The anchorage can be effected by edge teeth, in a solid embodiment with surface teeth, or with bone cement. The teeth can also be bioactive. In order to achieve the lordosis of the spinal column, the frontal edge of the shoulder is higher than the rear edge. The spacing piece shown in FIG. 2 has a convex center part 4, of which the radius of curvature exactly corresponds to the radius of curvature of the concave center portion 1 of the end plates. It is also provided with an annular, plane guide rim 5 and has a toroid 6 as a guard against a slip-out. Heightwise, the spacing piece can be designed according to the individual requirements of the space between the vertebrae. The spacing piece is made of a physiologically acceptable material, and, like the end plates, is also provided with a high polish in order to minimize abrasion.

The spacing piece can be provided with a radiologically visible marking.

Example 2

The end plates shown in FIGS. 4 and 5 are configured as already described in example 1, however, additionally, on both lateral sides, they are provided with laminar extensions. These laminar extensions can be made fitted to the curvature of the base plate of the vertebra body or the cover plate of the vertebra body.

The cavity below the plane guide rim 2 is filled with a disc 8 made of alloplastic material. It is also possible to fill this cavity with bone cement or to use a solid center portion from the outset.

The end plate is manufactured of a material which can be physiologically tolerated.

Example 3;

The end plates of a multiple-part intervertebral disc endoprothesis, as shown in FIGS. 8 and 9, are configured as so-called solid end plates 9. The concave center portion 1 and an annular groove 10 with an intermediate guide rim 2 are incorporated into the solid end plates 9. Teeth 3 are also provided. The curvature of the solid end plate 9 can correspond also to the curvature of the base plate of the vertebra body or the cover plate of the vertebra body.

Example 4

Figure 10:
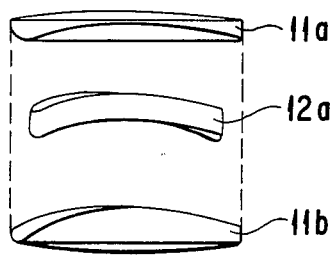
FIG. 10 is an exploded side elevation view of an intervertebral disc endoprothesis according to the invention wherein the planes of movement are rotated by 90°—embodiment 1.
Figure 11:
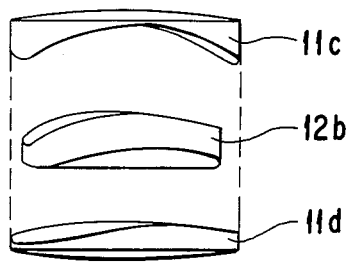
FIG. 11 is an exploded side elevation view of an intervertebral disc endoprothesis according to the invention wherein the planes of movement are rotated by 90°—embodiment 2.
Figure 10A:
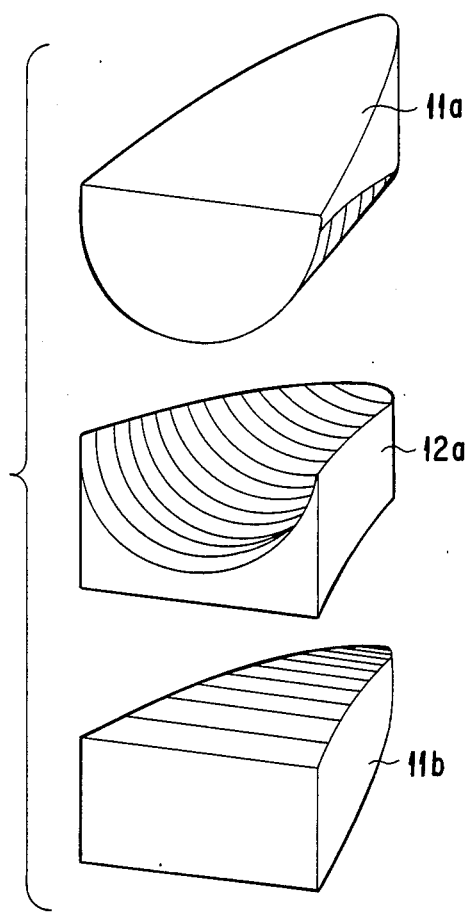
FIG. 10a is an elevated cross-section of the endoprosthesis shown in FIG. 10.

The intervertebral disc endoprothesis shown in FIG. 10 comprises somewhat oval or round end plates 11a and 11b of equal circumferences and a spacing piece 12a which is symmetrically smaller in relation to the end plates 11. The upper surface and the lower surface of the spacing piece 12a as well as the adjacent surfaces of the end plates 11a and 11b correspond to partial surfaces of a cylinder with in each case equal radius of curvature of parts which are articulated with each other, and their directions or surfaces of movement are offset in relation to each other by 90°. A cross-sectional view of the FIG. 10 endoprosthesis can be seen in FIG. 10a. FIG. 11 shows an endoprosthesis similar to FIG. 10, comprising end plates 11c and 11d and spacing piece 12b.

During functioning of this intervertebral disc endoprothesis, a rolling movement is performed in one of the areas of movement and a concurrent gliding movement in the other, whereby the spacing piece changes position during the movement process and the end plates remain stably anchored on the vertebrae bodies.

Example 5

The intervertebral disc endoprothesis shown in FIGS. 12 to 21 is configured as already described in example 4. Additionally, it has centrally positioned pins 13 extending in cranial and caudal directions. The pins 13 extend either into circular recesses 14, as shown in FIGS. 12 to 16, or into slot-shaped recesses 15, as shown in FIGS. 17 to 21. A reverse configuration of pins 13 and recesses 14, 15 is possible. In FIG. 12, the endoprosthesis includes end plates 11e and 11f with spacing piece 12c therebetween. In the FIG. 17 embodiment, spacing piece 12d is located between end plates 11g and 11h. The end plates and spacing piece of FIG. 17 are of the same construction and orientation as those in FIG. 12, and differ only in the type of recesses and pins employed.

Example 6

Figure 22:
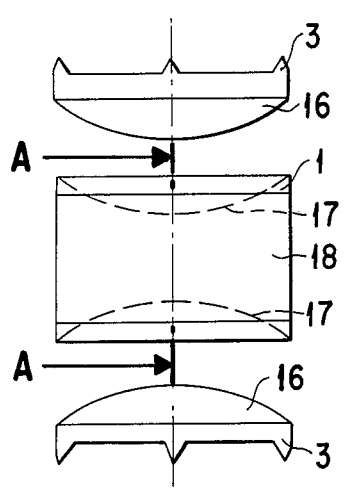
FIG. 22 is an exploded side elevation view of an intervertebral disc endoprothesis according to the invention, with convex end plates and cylindrical spacing piece which is concave at both ends.
Figure 24:
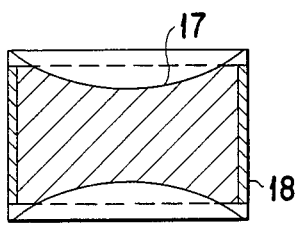
FIG. 24 is a cross-section through the cylindrical spacing piece of FIG. 21 taken on section line A—A of FIG. 21.

The intervertebral disc endoprothesis shown in FIGS. 22 and 24 comprises convex end plates 16 and a cylindrical spacing piece with concave ends 17. The spacing piece is enclosed in a rigid cover 18. The radii of curvature of the convex surfaces and the concave surfaces are equal. Heightwise, the cover is made smaller than the spacing piece in order to avoid contact with the end plates.

Example 7

Figure 23:
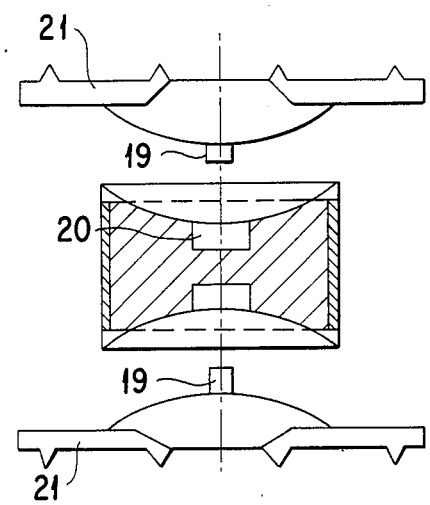
FIG. 23 is an exploded side elevation view of an intervertebral disc endoprothesis according to the invention, similar to that of FIG. 22, however, with additional safeguard pins.

The intervertebral disc endoprothesis shown in FIG. 23 is configured as in example 6. Additionally, the convex end plates 16 are provided with pins 19 pointing in cranial or caudal direction. The pins 19 engage in the circular openings 20. The openings 20 have a greater diameter than the pins 19.

Example 8

Figure 25:
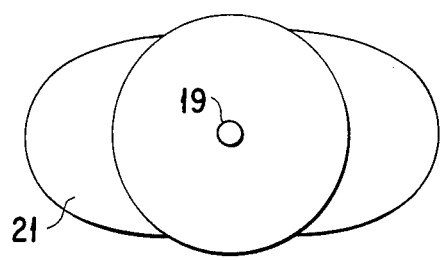
FIG. 25 is a top plan view of an intervertebral disc endoprothesis according to the invention, similar to FIG. 22, however, with additional lateral extensions.

The intervertebral disc endoprothesis is configured either as described in either example 6 or 7. Additionally, the convex end plates 16 have on both sides lateral extensions 21, as illustrated in FIGS. 23 and 25.

We claim:

1. Intervertebral disc endoprosthesis comprising first and second end plates and a spacing piece, said spacing piece having top and bottom surfaces, said first end plate having a first surface adjacent the top surface of said spacing piece and said second end plate having a second surface adjacent the bottom surface of said spacing piece, said top, bottom, first and second surfaces each being partial surfaces of a cylinder, said top surface and said first surface adjacent the top surface being congruent and defining a first cylinder-shaped movement surface and said bototm surface and said second surface adjacent the bototm surface being congruent and defining a second cylinder-shape movement surface, said first and second movement surfaces being rotationally-offset 90° with respect to each other about a central axis passing through said spacing piece and said end plates.

2. Intervertebral disc endoprothesis according to claim 1 further comprising respective pins cranially and caudally extending from the spacing piece and a recess in each of the end plates each receiving a respective one of the pins.

* * * * *